United States Patent [19]
De Simone et al.

[11] 4,117,249
[45] Sep. 26, 1978

[54] ACETYLENIC ALCOHOLS, THEIR DERIVATIVES AND PROCESS FOR THEIR PRODUCTION

[75] Inventors: Renato De Simone, Como; Edoardo Platone; Morello Morelli, both of San Donato Milanese (Milan), all of Italy

[73] Assignee: Anic, S.p.A., Palermo, Italy

[21] Appl. No.: 698,812

[22] Filed: Jun. 23, 1976

[30] Foreign Application Priority Data

Jun. 24, 1975 [IT] Italy ................................ 24704 A/75

[51] Int. Cl.$^2$ ........................ C07C 33/04; C11D 1/68; C11D 1/75
[52] U.S. Cl. ................................ 568/855; 252/89 R; 260/615 B; 260/615 R; 568/852; 568/857; 568/861
[58] Field of Search ..................................... 260/635 Y

[56] References Cited

U.S. PATENT DOCUMENTS

| | | | |
|---|---|---|---|
| 2,863,929 | 12/1958 | Lowell | 260/635 Y |
| 2,997,447 | 8/1961 | Russell et al. | 260/635 Y |
| 3,293,191 | 12/1966 | Carpenter et al. | 260/635 Y |
| 3,626,016 | 12/1971 | Martin | 260/635 Y |

FOREIGN PATENT DOCUMENTS

364,500  9/1962  Switzerland .......................... 260/635 Y

OTHER PUBLICATIONS

Bennett, "Chem. Abstracts", vol. 83 (1975), p. 390, item 192500w.
"Chem. Abstracts", vol. 83 (1975), Chemical Substance Index (C–H) 1852cs.
Reppe "Advances in Acetylene Chemistry", (1946), Title page, pp. 1, 13, 14 and 15.

*Primary Examiner*—Joseph E. Evans
*Attorney, Agent, or Firm*—Morgan, Finnegan, Pine, Foley & Lee

[57] ABSTRACT

The invention relates to acetylenic glycols having the formula:

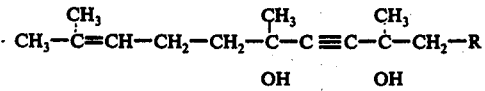

wherein R is hydrogen or an alkenyl group, and to their derivatives obtained through hydrogenation or ethoxylation reactions, these compounds showing outstanding surface active properties. The invention relates also to the process for the preparation of the subject compounds starting from 6-methyl-5-hepten-2-one.

1 Claim, No Drawings

ACETYLENIC ALCOHOLS, THEIR DERIVATIVES AND PROCESS FOR THEIR PRODUCTION

The present invention relates to novel acetylenic tertiary glycols, to their derivatives and to the process for their preparation.

More particularly, the invention relates to the acetylenic glycols having the formula

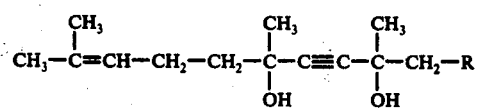

wherein R can be hydrogen or an alkenyl radical, and to the compounds obtainable therefrom through selective reactions involving the unsaturated bonds or the hydroxyls.

Two particular compounds shall be hereinafter described, which correspond to the above formula, as well as some compounds obtainable therefrom, in order to permit a better understanding of the subject of the invention.

However, any possible variation shall be considered within the scope of the present invention, when leading to formulas falling in the more general formula hereinbefore referred to, since it seems rather simple for every person skilled in the art to achieve them through obvious means and modifications of the preparation reactions as hereinafter described.

The following compounds shall be thus illustrated:

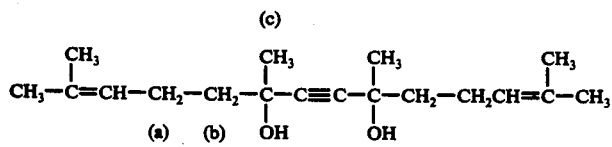

2, 6, 9, 13-tetramethyl-2,12-tetradecadien-7-in-6-9-diol and

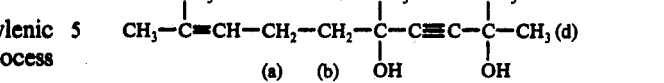

2, 6, 9-trimethyl-2-decen-7 - in - 6,9 - diol, and some compounds which can be derived therefrom.

Amongst the latter:

(a) the compounds obtainable, both from II and from III, through selective partial hydrogenation of the triple bond to an olefinic bond:

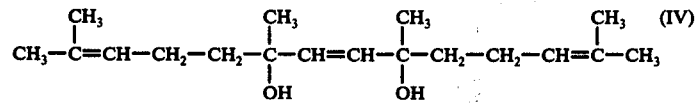

2, 6, 9, 13 - tetramethyl - 2, 7, 12 - tetradecatrien - 6, 9-diol, and

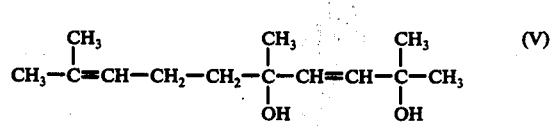

2, 6, 9 - trimethyl - 2,7- decadien- 6, 9 - diol (b) the compounds obtainable; both from II and from III, through complete hydrogenation both of the triple bond and of the double bonds:

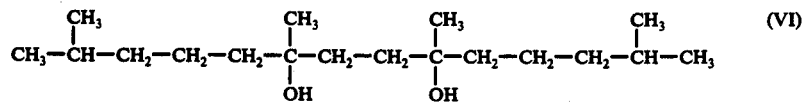

2, 6, 9, 13 - tetramethyl-tetradecan - 6, 9- diol, and

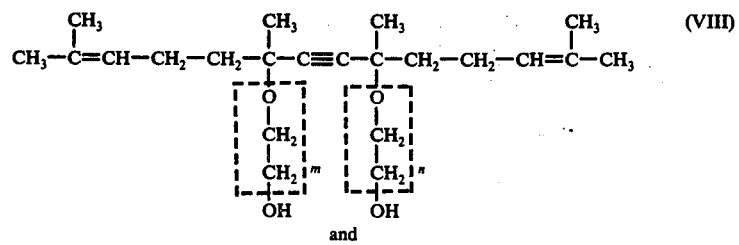

2, 6, 9 - trimethyl-decan-6, 9 - diol (c) the compounds obtainable from all the aforementioned compounds (II to VII) through ethoxylation reactions on both the hydroxyls of each molecule, e.g.:

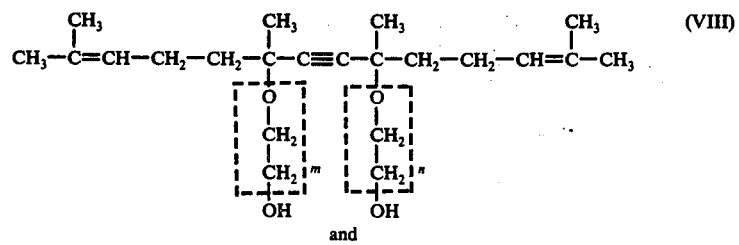

and

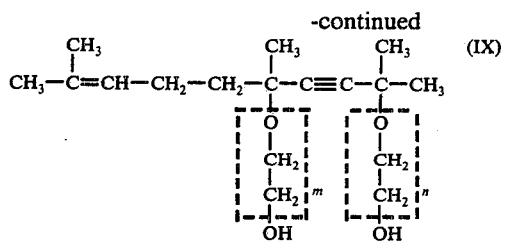

wherein M + n = 3 ÷ 30 molecules of ethylene oxide and similarly starting from IV, V, VI and VII (the compounds X, XI, XII and XIII, being respectively obtained).

The identification of the two acetylenic glycols II and III was carried out by means of IR, NMR and GLC - mass analyses.

More particularly the following IR bands were found:
Compound II: 3390; 3050; 1674; 1124 cm$^{-1}$
Compound III: 3380; 3030; 1670; 1163 cm$^{-1}$
and the following characteristic NMR signals (solvent: CCl$_4$; internal standard: HMDS):

| Compound II | =CH | 5.07 ppm |
| --- | --- | --- |
| | —OH | 3.48 |
| | —CH$_2$ (a) | 2.11 |
| | =C$\diagup^{CH_3}_{\diagdown CH_3}$ | 1.58 |
| | —CH$_2$ (b) | ~1.58 |
| | —CH$_3$ (c) | 1.36 |
| Compound III | =CH | 5.08 ppm |
| | —OH | 4.52 |
| | —CH$_2$ (a) | 2.06 ppm |
| | =C$\diagup^{CH_3}_{\diagdown CH_3}$ | 1.58 |
| | —CH$_2$ (b) | ~1.58 |
| | —CH$_3$ (c) | 1.41 |
| | —CH$_3$ (d) | 1.38 |

The compounds II and III are furthermore characterized by the following chemical and physical data:

| | | II | III |
| --- | --- | --- | --- |
| boiling point, | ° C | 168 (at 0.25 mmHg) | 112 (at 0.6 mm Hg) |
| melting point, | ° C | ~51 | |
| density | | 0.904 at the melting point | 0.920 at 27° C |

Both compounds are soluble in all the common organic solvents and show high thermal stability. The compounds II and III show, moreover, the following values of surface tension τ in aqueous solutions, as determined according to the method of Lecomte de Noüy:

| Compound | Concentration in aqueous solution - % by weight | τ at 25° C, dynes/cm |
| --- | --- | --- |
| | 0.005 | 34.7 |
| II | 0.01 | 33.8 |
| | 0.02 | 33.0 |
| | 0.03 | 32.5 |
| | 0.005 | 69.4 |
| | 0.01 | 65.8 |
| III | 0.02 | 59.3 |
| | 0.03 | 57.5 |
| | 0.04 | 53.2 |

| Compound | Concentration in aqueous solution - % by weight | τ at 25° C, dynes/cm |
| --- | --- | --- |
| | 0.05 | 51.5 |

The acetylenic glycols according to the formulas II and III are useful as surface active agents and are moreover adapted to be used, both alone and in admixture amongst themselves or with other known compounds (e.g. ethylene glycol, etc.) as wetting agents, dispersants, anti-foaming non-ionic agents, viscosity stabilizers and as intermediates for novel compounds.

The compounds IV, V, VI and VII can find use as surface active agents, wetting agents and anti-foaming compounds. The compounds of the type VIII and IX, the water solubility of which increases as the number of moles of ethylene oxide is increased, are useful as non-ionic surface active agents, wetting, anti-foaming and emulsioning agents for particular uses, as well as antistatic lubricants in the spinning of fibres.

Specific property of all the above mentioned compounds, when used as surface active agents, is the low concentration at which their use in aqueous solution is possible with good results, these results being achieved by other known compounds only at higher concentrations.

It is to be lastly pointed out that all the above listed compounds are useful as intermediates in a great number of synthesis processes for several organic compounds.

The compounds II and III, particularly, can be prepared according to the operating conditions as described in the following Examples.

These Examples relate to preparing processes carried out essentially starting from 6-methyl-5-hepten-2-one; it is anyhow evident that like reactions starting from isomers of the same compound can be equally carried out, always remaining in the scope of the invention, compounds having the backbone of the compound I, but with "shifted" double bonds being obtained, (e.g. starting from 6-methyl-6-hepten-2-one compounds are obtained according to the formulas II and III in which the double bonds in 2, 12 and in 2 are displaced in the positions 1, 13 and 1, respectively).

EXAMPLE I

A mixture of 112 g (2.0 moles) of powdery KOH in 600 mls of tetrahydrofuran, previously saturated with acetylene, is supplemented at 30°–40° C with 126 g (1.0 mole) of 6-methyl-5-hepten-2-one (ME)

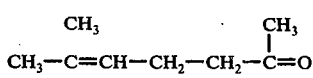

the addition being effected dropwise and over about 1 hour.

The mixture is then maintained under stirring for further about 3 hours at 45° C, with a constant overpressure of acetylene of 150 to 200 mm Hg. The mixture is then neutralized with a mixture of concentrated HCl-ice up to a pH = 6, 7; it is extracted with ether, dried over anhydrous $MgSO_4$ and the ether is evaporated. The residue contains a mixture of the compound II and of dehydrolinalool (DHL):

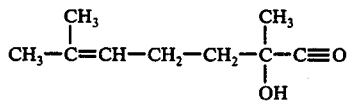

besides the unreacted ME.

ME conversion: 66.3%; molar selectivity as compound II: 38%; molar selectivity as DHL: 35%.

The compound II can be thereafter obtained at a high purity degree by vacuum distillation of the reaction stock, possibly followed by low temperature crystallization from a number of solvents.

EXAMPLE 2

The preceding Example is repeated apart from the following variations:

5 g (0.08 moles) of KOH
200 mls of anhydrous dimethylsulfoxide
63 g (0.5 mole) of ME At the end the ME conversion is 76%, the molar selectivity as the compound II is 37% and that as DHL is 59%.

EXAMPLE 3

The reaction can be carried out with ME and DHL + KOH in almost stechiometrical ratios (K-alcoholate) in several solvents (e.g. tetrahydrofurane, dimethylsulfoxide, dimethylformamide, dimethyl acetamide, N-methylpyrrolidone, etc.) without acetylene, in conditions like to the preceding ones.

EXAMPLE 4

By carrying out the synthesis of the DHL with ME, acetylene and KOH in stechiometrical ratios using liquid $NH_3$ as the solvent, with a $ME/C_2H_2$ ratio = 1 mol and at temperatures of 20° to 60° C, a mixture of compound II and DHL is obtained.

The compound II can be then almost quantitatively recovered by distilling the residual bottoms of the distillation of the reaction mixture, after DHL has been obtained as the head product.

EXAMPLE 5

From ME, acetone and acetylene, by operating like the Examples 1 and 2, the compound III is obtained, in admixture with methylbutynol.

The compound III can be likely obtained from ME, acetone and acetylene, using liquid $NH_3$ as the solvent, and KOH in stechiometrical amount or otherwise from DHL + KOH (alcoholate) or from methylbutynol + KOH (alcoholate) and ME, in the absence of acetylene, in several aprotic solvents.

The preparation of the other compounds referred to (from IV to XIII) can be effected starting from the compounds II and III by means of essentially known reactions.

For example:

(a) selective hydrogenation of the triple bond of the compounds II and III to an olefinic bond with partially poisoned catalysts (e.g. Pd/$CaCO_3$ with Zn $(CH_3COO)_2.2H_2O$) for the preparation of the compounds IV and V;

(b) complete hydrogenation of all the unsaturated bonds present in the compounds II and III, by means of ordinary not inhibited hydrogenation catalysts, for the compounds VI and VII;

(c) reaction of the compounds II to VII with ethylene oxide, for the compounds VIII to XIII.

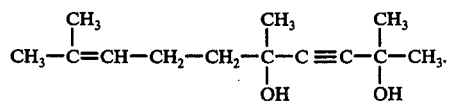

I claim:
1.